US009857347B2

(12) United States Patent
Basheer et al.

(10) Patent No.: US 9,857,347 B2
(45) Date of Patent: *Jan. 2, 2018

(54) N-NITROSAMINE DETERMINATION IN AQUEOUS SAMPLES WITH SONICATION AND MICROEXTRACTION

(71) Applicant: KING FAHD UNIVERSITY OF PETROLEUM AND MINERALS, Dhahran (SA)

(72) Inventors: Chanbasha Basheer, Dhahran (SA); Mousa Yaser Amayreh, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,812

(22) Filed: Jun. 27, 2017

(65) Prior Publication Data

US 2017/0292939 A1     Oct. 12, 2017

Related U.S. Application Data

(63) Continuation of application No. 15/065,480, filed on Mar. 9, 2016.

(51) Int. Cl.
| | | |
|---|---|---|
| *G01N 33/18* | (2006.01) | |
| *G01N 1/40* | (2006.01) | |
| *G01N 30/72* | (2006.01) | |
| *G01N 30/88* | (2006.01) | |
| *G01N 35/10* | (2006.01) | |
| *G01N 30/24* | (2006.01) | |
| *G01N 30/06* | (2006.01) | |
| *G01N 30/02* | (2006.01) | |
| *G01N 35/00* | (2006.01) | |

(52) U.S. Cl.
CPC ..... *G01N 33/1826* (2013.01); *G01N 30/7206* (2013.01); *G01N 30/88* (2013.01); *G01N 35/1095* (2013.01); *G01N 2001/4061* (2013.01); *G01N 2030/062* (2013.01); *G01N 2030/884* (2013.01); *G01N 2035/00554* (2013.01); *G01N 2035/1034* (2013.01); *Y10T 436/170769* (2015.01); *Y10T 436/173845* (2015.01); *Y10T 436/24* (2015.01); *Y10T 436/255* (2015.01)

(58) Field of Classification Search
CPC ......... G01N 1/4055; G01N 2001/4061; G01N 2030/062; G01N 30/06; G01N 30/72; G01N 30/7206; G01N 2030/025; G01N 2030/065; G01N 2030/884; G01N 30/24; G01N 30/88; G01N 33/1826; G01N 35/1095; G01N 2035/1034; G01N 2035/00554; Y10T 436/11; Y10T 436/17; Y10T 436/170769; Y10T 436/173845; Y10T 436/203332; Y10T 436/204165; Y10T 436/212; Y10T 436/214; Y10T 436/216; Y10T 436/24; Y10T 436/25; Y10T 436/25375; Y10T 436/255
USPC ... 436/43, 45, 106, 107, 111, 127, 131, 132, 436/139, 140, 141, 142, 161, 173, 174, 436/177, 178; 422/63, 68, 1, 89, 527, 422/533
See application file for complete search history.

(56) References Cited

U.S. PATENT DOCUMENTS

| 9,128,106 B2 | 9/2015 | Basheer et al. |
| 9,212,979 B2 | 12/2015 | Chanbasha |

FOREIGN PATENT DOCUMENTS

| CN | 103217497 A | 7/2013 |
| CN | 102692474 B | 8/2014 |

OTHER PUBLICATIONS

Vazquez et al. Journal of Chromatography A, vol. 1291, Mar. 29, 2013, pp. 19-26.*
Amayreh, M., et al. "Determination of N-Nitrosamines by Automated Dispersive Liquid-Liquid Microextraction Integrated with Gas Chromatography and Mass Spectrometry", Journal of Separation Science, vol. 38, No. 10, pp. 1741-1748, (Mar. 9, 2015).
Khodadoust, S., et al., "Application of Response Surface Methodology for Determination of Methyl Red in Water Samples by Spectrophotometry Method.", Spectrochimica ACTA Part A: Molecular and Biomolecular Spectroscopy, vol. 133, 1 Page total (Apr. 30, 2014) (Abstract only).
Niazi, A., et al., "Spectrophotometric Determination of Bismuth in Water Samples by Dispersive Liquid-Liquid Microextraction after Multivariate Optimization based on Box-Behnken", Journal of the Chilean Chemical Society, vol. 58, No. 3, pp. 1899-1901, (2013).
Li, S., et al., "Extensible Automated Dispersive Liquid-Liquid Microextraction", Analytica Chimica ACTA, 3 Pages total, (Feb. 27, 2015) (Abstract only).
Llop, A., et al., "Fully Automated Determination of N-Nitrosamines in Environmental Waters by Headspace Solid-Phase Microextraction followed by GC-MS-MS", Journal of Separation Science, vol. 33, pp. 3692-3700 (2010).

(Continued)

Primary Examiner — Maureen Wallenhorst
(74) Attorney, Agent, or Firm — Oblon, McClelland, Maier & Neustadt, L.L.P.

(57) ABSTRACT

An automated dispersive liquid-liquid microextraction method of detecting and quantifying N-nitrosamines in an aqueous sample. The method includes (a) extracting an aqueous solution including the N-nitrosamines by mixing an extraction solvent and a dispersive solvent with the aqueous solution, such that the N-nitrosamines, or a portion thereof, re-distribute from the aqueous solution to the extraction solvent, (b) permitting the resulting mixture in (a) to form a two-phase mixture containing an aqueous phase containing the aqueous solution with reduced amounts of the N-nitrosamines and an organic phase including the extraction solvent with the N-nitrosamines extracted from the aqueous solution, (c) injecting the organic phase, or a portion thereof, into an injection port of a gas chromatograph coupled with at least one mass spectrometer, and (d) analyzing the N-nitrosamines by gas chromatography and mass spectrometry to detect and quantify the concentration of the N-nitrosamines in the aqueous solution.

16 Claims, 5 Drawing Sheets

(56) References Cited

OTHER PUBLICATIONS

Farajzadeh, M.A., et al., "Dispersive Liquid-Liquid Microextraction using Extraction Solvent Lighter than Water", Journal of Separation Science, vol. 32, pp. 3191-3200, (2009).
Ramezani et al. European Food Research Technology, vol. 240, Oct. 4, 2014, pp. 441-450.
Anthemidis et al. Talanta, vol. 79, pp. 86-91, 2009.
Campillo et al. Journal of Chromatography A, vol. 1218, 2011, pp. 1815-1821.
Ojeda et al. Chromatographia, vol. 69, No. 11/12, Jun. 2009, pp. 1149-1159.

* cited by examiner

N-NITROSAMINE DETERMINATION IN AQUEOUS SAMPLES WITH SONICATION AND MICROEXTRACTION

CROSS-REFERENCE TO RELATED APPLICATIONS

The present application is a continuation of Ser. No. 15/065,480, having a filing date of Mar. 9, 2016, now U.S. Pat. No. 9,759,705.

This application incorporates by reference in their entirety U.S. Pat. No. 9,128,106 B2, issued Sep. 8, 2015, and the following publication: Determination of N-nitrosamines by automated dispersive liquid-liquid microextraction integrated with gas chromatography and mass spectrometry, Mousa Amayreh, Basheer Chanbasha, Khalid Alhooshani, Nuhu Dalhat Mu'azu, and Hian Kee Lee, J. *Sep. Sci.* 2015, 38, 1741-1748.

BACKGROUND OF THE INVENTION

Technical Field

The present disclosure relates to the field of a dispersive liquid-liquid microextraction technique, particularly an automated dispersive liquid-liquid microextraction method of detecting and quantifying one or more N-nitrosamines in an aqueous solution.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, is neither expressly nor impliedly admitted as prior art against the present invention.

N-nitrosamines (NAs) are a class of organic compounds derived from the reaction of amines (secondary amines) with nitrosating agents (Llop, A., Borrull, F., Pocurull, E., J. Sep. Sci. 2010, 33, 3692-3700.4; Llop, A., Pocurull, E., Borrull, F., J. Chromatogr. A 2010, 1217, 575-581—each incorporated herein by reference in its entirety). Examples of NAs include N-nitroso-di-n-propylamine (NDPA), N-nitrosopiperidine (NPIP), N-nitroso-di-n-butylamine (NDBA), N-nitrosodiethylamine (NDEA), N-nitrosodimethylamine (NDMA), N-nitroso-di-n-phenylamine (NDPhA), N-nitrosomethylethylamine (NMEA), N-nitrosomorpholine (NMOR), and N-nitrosopyrrolidine (NPYR). NAs are classified as potentially hazardous disinfection by-products (DBPs) produced through a chlorine or ozone based disinfection processes of drinking water (Wang, W., Ren. S., Zhang, H., Yu. Y., An. W., Hu. J., Yang. M., Water Res. 2011, 45, 4930-4938; Ripolles, C., Pitarch, E., Sancho, J. V., Lopez, F. J., Hernandez, F., Anal. Chem. Acta 2011, 702, 62-71.—incorporated herein by reference in its entirety). NAs are also present in other anthropogenic sources such as polymer waste, plasticizers, rocket fuel (incomplete oxidation of hydrazines), batteries and other industrial products.

Due to their polarity, NAs are usually soluble in water, and are detected in a wide range of sample matrices which include drinking, ground, waste and treated wastewater samples (Anna, V., Rimma, S., Ovadia, L., Jenny, G., Anal. Chim. Acta. 2011, 685, 162-169; Richardson, S. D., Anal. Chem. 2009, 81, 4645-4677—each incorporated herein by reference in its entirety), soils (Pan, X., Zhang, B., Cox, S. B., Anderson, T. A., Cobb, G. P., J. Chromatogr. A 2006, 1107, 2-8—incorporated herein by reference in its entirety), cosmetics (Qiang, M., Hai-Wei, X., Chao, W., Hua, B., Guang-Cheng, X., Ning, S., Li-Yan, X., Jun-Bing, W Chin. J. Anal. Chem. 2011, 39, 1201-1207; Schothorst, R. C., Somers, H. H. J., Anal. Bioanal. Chem. 2005, 381, 681-685; Flower, C., Carter, S., Earls, A., Fowler, R., Hewlins, S., Lalljie, S., Lefebvre, M., Mavro, J., Small, D., Volpe, N., Int. J. Cosmet. Sci. 2006, 28, 21-33—each incorporated herein by reference in its entirety), biological samples (urine, saliva, blood), and tobacco smoke (Ramrez, N., Ozel, M., Lewis, A., Marce, M., Borrull, F., Hamilton, J. Chromatogr. A 2012, 1219, 180-187—incorporated herein by reference in its entirety). Trace amounts of NAs have also been detected in many food products, such as bacon (Ventanas. S, Ruiz. J., Talanta 2006, 70, 1017-1023—incorporated herein by reference in its entirety), fish and beer (Sanches, P. J. F., Zanin, K. E., Camarão, E. B., Garcia, R. C., Rios, A., Valcarcel, M., Quimica Nova 2003, 193-196; Mendez, D., Gonzalez, G., Botello, E., Escamilla, E., Alvarado, J. F. J., Food Chem. 2008, 107, 1348-1352—each incorporated herein by reference in its entirety), meat (Campillo, N., Vinas, P., Martnez-Castillo, N., Hernndez-Crdoba, M., J. Chromatogr. 2011, 1218, 1815-1821—incorporated herein by reference in its entirety), and frankfurters and sausages (Oliveira, C. P., Gloria, M. B. A., Barbuor, J., Scalan, R. A., J. Agric. Food Chem. 1995, 43, 967-969—incorporated herein by reference in its entirety).

NAs are receiving special attention due to high toxicity effects and due to their ability to enhance tumors in various animal and human species (Yurchenko, S., Molder, U., Food Chem. 2006, 96, 325-333; Andrade, R., Reyes, F. G. R., Rath, S., Food Chem. 2005, 91, 173-179; Andrade, R., Reyes, F. G. R., Rath, S., Food Chem. 2005, 91, 173-179—each incorporated herein by reference in its entirety). The US Environmental Protection Agency (EPA) has classified N-nitrosamines in the B2 group as probable human carcinogens, and has also established ng/L control levels in drinking water. As a result, the maximum admissible concentrations of selected N-nitrosamines in water at a risk estimation of $10^{-4}$ are 20, 70, 600, 2,000, and 700,000 ng/L for NDEA, NDMA, NDBA, NPYR, and NDPhA, respectively.

The most common analytical methods used for determination of NAs are (i) colorimetry (Jurado-Sanchez, B., Ballesteros, E., Gallego, M., Talanta 2007, 73, 498-504—incorporated herein by reference in its entirety), (ii) capillary electro-chromatography (CE) (Matyska, M. T., Pesek, J. J., Yang, L., J. Chromatogr. A 2000, 887, 497-503—incorporated herein by reference in its entirety), (iii) micellar electrokinetic capillary chromatography (MECC) (Filho, P. J. S., Rios, A., Valcarcel, M., Caramao, E. B., Water Res. 2003, 37, 3837-3842—incorporated herein by reference in its entirety), (iv) gas chromatography (GC) with a different detector such as a flame ionization detector (FID) (Jurado-Sanchez, B., Ballesteros, E., Gallego, M., J. Chromatogr A, 2007, 1154, 66-73—incorporated herein by reference in its entirety), a nitrogen phosphorous detector (NFD) (Andrade, R., Reyes, F. G. R., Rath, S., Food Chem. 2005, 91, 173-179—incorporated herein by reference in its entirety), a thermal energy detector (TED) (Incavo, J. A., Schafer, M. A., Anal. Chim. Acta, 2006, 557, 256-261—incorporated herein by reference in its entirety), a nitrogen chemiluminescence detector (NCD) (Ozel, M. Z., Gogus, F., Yagci, S., Hamilton, J. F., Lewis, A. C., Food Chem. Toxicol. 2010, 48, 3268-3273—incorporated herein by reference in its entirety), and with mass spectrometry detectors (MSDs) (Anna, V., Rimma, S., Lev, O., Jenny, G., Anal. Chim. Acta.

2011, 685, 162-169—incorporated herein by reference in its entirety). Recently, high-performance liquid chromatography (HPLC) methods with different detectors, such as MSDs (Xiong W, Hou H W, Jiang X Y, Tang G L, Hu Q Y. Anal. Chim. Acta, 2010, 674(1): 71-78—incorporated herein by reference in its entirety), ultra violet detectors (UVD) (Kodamatani, H., Yamazaki, S., Saito, K., Amponsaa-Karikari, A., Kishikawa, N., Kuroda, N., Tomiyasu, T., Komatsu, Y., J. Chromatogr. A 2009, 1216, 92-98—incorporated herein by reference in its entirety), and fluorescence detectors (FD) (Zhao, Y.-Y., Boyd, J., Hrudey, S. E., Li, X.-F., Environ. Sci. Technol. 2006, 40, 7636-7641—incorporated herein by reference in its entirety), were used for the analysis of NAs. Analysis of NAs by using GC is more sensitive than HPLC methods (Krauss, M., Hollender, J., Anal. Chem. 2008, 80, 834-842; Plumlee, M., Lo'pez-Mesas, M., Heidlberger, A., Ishida, K. P., Reinhard, M., Water Res. 2008, 42, 347-355—incorporated herein by reference in its entirety).

Since the concentrations of NAs in chlorinated drinking water and in chlorine treated waste water are usually less than 10 ng/L and at or over 100 ng/L, respectively, NAs need to be determined at low ng/L levels in water samples, especially drinking water, so enrichment techniques are preferred or even mandatory. Dispersive liquid-liquid microextraction (DLLME) is a simple, rapid, and low cost pre-concentrating technique with high recovery rates and enrichment factors. In DLLME, a solvent mixture (water immiscible extraction solvent and water-miscible dispersive solvent) is injected rapidly into the aqueous sample. The combination of this solvent mixture produces fine droplets instantaneously; the extraction solvent containing the analytes is then isolated as a separate layer, collected, and analyzed.

In view of the forgoing, the present disclosure relates to an automated dispersive liquid-liquid microextraction method for detecting and quantifying one or more N-nitrosamines in an aqueous solution. The automated DLLME method may use a CombiPAL autosampler coupled with GC-MS for the determination of NAs. The disclosed method advantageously minimizes human exposure to harmful NAs and to extraction and dispersive solvents that may be toxic.

BRIEF SUMMARY OF THE INVENTION

The present disclosure relates to an automated dispersive liquid-liquid microextraction method for detecting and quantifying one or more N-nitrosamines in an aqueous solution. The method includes (a) extracting an aqueous solution comprising the one or more N-nitrosamines by mixing an extraction solvent and a dispersive solvent with the aqueous solution, such that the one or more N-nitrosamines, or a portion thereof, re-distribute from the aqueous solution to the extraction solvent, (b) permitting the resulting mixture in (a) to form a two-phase mixture comprising an aqueous phase comprising the aqueous solution with reduced amounts of the one or more N-nitrosamines and an organic phase comprising the extraction solvent with the one or more N-nitrosamines extracted from the aqueous solution, (c) injecting the organic phase, or a portion thereof, into an injection port of a gas chromatograph coupled with at least one mass spectrometer, and (d) analyzing the one or more N-nitrosamines by gas chromatography and mass spectrometry to detect and quantify the concentration of the one or more N-nitrosamines in the aqueous solution.

In one or more embodiments, the aqueous solution in (a) comprises at least one selected from the group consisting of tap water, well water, ground water, river water, waste water, and water treated with chlorine and/or ozone.

In one or more embodiments, the aqueous solution in (a) has a pH between 9.5 and 11.5.

In one or more embodiments, the aqueous solution in (a) comprises about 20-25% by weight/volume of sodium chloride.

In one or more embodiments, the one or more N-nitrosamines present in the aqueous solution in (a) are not derivatized.

In one or more embodiments, the one or more N-nitrosamines are selected from the group consisting of N-nitroso-di-n-propylamine (NDPA), N-nitrosopiperidine (NPIP), N-nitroso-di-n-butylamine (NDBA), N-nitrosodiethylamine (NDEA), N-nitrosodimethylamine (NDMA), N-nitroso-di-n-phenylamine (NDPhA), N-nitrosomethylethylamine (NMEA), N-nitrosomorpholine (NMOR), N-nitrosopyrrolidine (NPYR), and a combination thereof.

In one or more embodiments, in (a) the extraction solvent and the dispersive solvent are added to the aqueous solution together as a pre-formed mixture in an automated fashion.

In one or more embodiments, in (a) the addition of the extraction solvent to the aqueous solution occurs prior to the addition of the dispersive solvent to the aqueous solution. In some embodiments, in (a) the addition of the extraction solvent to the aqueous solution is manual whereas the addition of the dispersive solvent to the aqueous solution is automated.

In one or more embodiments, the extraction solvent is at least one selected from the group consisting of cyclohexane, hexane, isooctane, n-pentane, toluene, p-xylene, a xylene isomers mixture, dibutyl ether, and mesitylene, or at least one selected from the group consisting of chlorobenzene, carbon tetrachloride, carbon dichloride, chloroform, and tetrachloroethylene.

In one or more embodiments, the dispersive solvent is at least one selected from the group consisting of methanol, ethanol, acetonitrile, and acetone.

In one or more embodiments, in (a) the extraction solvent comprises p-xylene and the dispersive solvent comprises methanol, and the volume ratio of the extraction solvent to the dispersive solvent ranges from 40:1 to 25:1.

In one or more embodiments, mixing the extraction solvent and the dispersive solvent with the aqueous solution in (a) comprises agitating the mixture of the extraction solvent, the dispersive solvent, and the aqueous solution. In some embodiments, the speed of the agitating is between 700 and 750 rotations per minute. In other embodiments, the duration of the agitating is between 25 and 30 minutes.

In one or more embodiments, mixing the extraction solvent and the dispersive solvent with the aqueous solution in (a) comprises sonicating the mixture of the extraction solvent, the dispersive solvent, and the aqueous solution at an effective power level and for an effective period of time.

In one or more embodiments, in (a) at least about 90% of the one or more N-nitrosamines re-distribute from the aqueous solution to the extraction solvent during the extracting.

In one or more embodiments, in (b) the resulting mixture forms a two-phase mixture by centrifuging the resulting mixture.

In one or more embodiments, the injecting produces a detection signal and the magnitude of the detection signal from the gas chromatography and mass spectrometry linearly correlates with the concentration of the one or more N-nitrosamines ranging from 0.1 to 100 μg/L.

In one or more embodiments, the gas chromatograph and mass spectrometer have a detection limit for detecting and quantifying the concentration of the one or more N-nitrosamines in the aqueous solution, which is between 5.7 and 52 ng/L.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
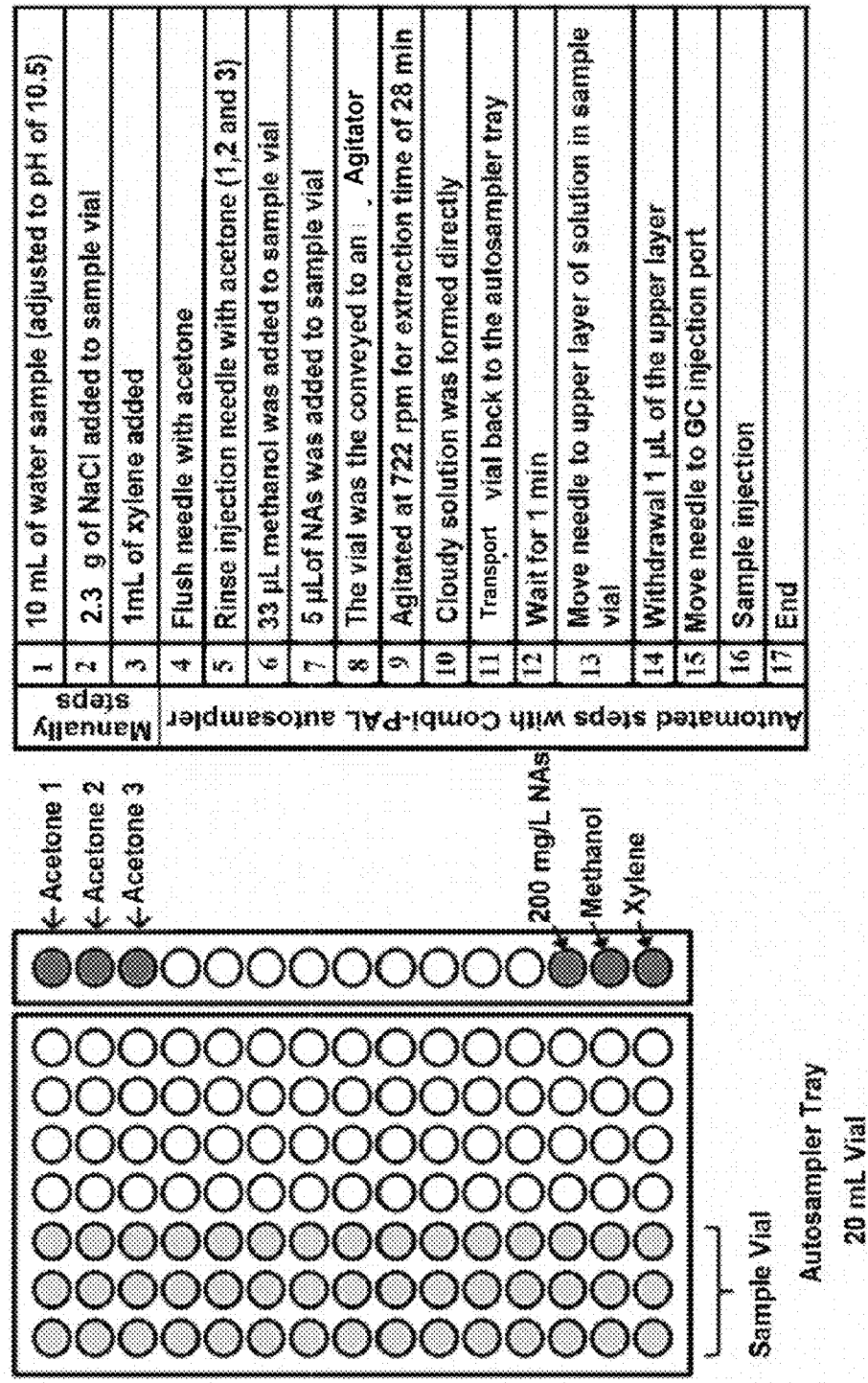
FIG. 1 is a schematic diagram of an autosampler tray with the sample vials layout and a chart showing the procedure of the automated DLLME technique for the analysis of N-nitrosamines in an aqueous solution.

Disclosed herein is an automated dispersive liquid-liquid microextraction method for detecting and quantifying one or more N-nitrosamines in an aqueous solution. The method includes (a) extracting an aqueous solution comprising the one or more N-nitrosamines by mixing an extraction solvent and a dispersive solvent with the aqueous solution, such that the one or more N-nitrosamines, or a portion thereof, re-distribute from the aqueous solution to the extraction solvent, (b) permitting the resulting mixture in (a) to form a two-phase mixture comprising an aqueous phase comprising the aqueous solution with reduced amounts of the one or more N-nitrosamines and an organic phase comprising the extraction solvent with the one or more N-nitrosamines extracted from the aqueous solution, (c) injecting the organic phase, or a portion thereof, into an injection port of a gas chromatograph coupled with at least one mass spectrometer, and (d) analyzing the one or more N-nitrosamines by gas chromatography and mass spectrometry to detect and quantify the concentration of the one or more N-nitrosamines in the aqueous solution.

In some embodiments, the aqueous solution in (a) comprises at least one selected from the group consisting of tap water, well water, ground water, river water, waste water, and water treated with chlorine and/or ozone.

In the method, an aqueous solution is analyzed for the nitrosamine content. The nitrosoamine content is preferably in the range of 0.1 to 100 µg/L. An aqueous solution containing NAs of higher than 100 µg/L is preferably diluted with water to have a diluted concentration of the NAs within the preferred range of 0.1-100 µg/L. Prior to the analysis, the aqueous solution may be handled and prepared using manual methods of mixing, including but not limited to, swirling the solution by hand, and by placing a magnetic stir bar in the solution and stirring with a magnetic stir plate. Mechanical methods include, but are not limited to, sonicating the solution using an ultrasonic bath or an ultrasonic probe. Preferably, the mixing is performed by swirling the solution by hand.

The volume of the aqueous solution in the method can vary, depending on, for example, the volume of the aqueous solution available, the instruments used, e.g. the size of the sample vials on an autosampler tray, and the initial concentrations of the N-nitrosamines in the aqueous solution. Generally, there is a desirable volume resulting in the maximal recovery rate and enrichment factor. In some embodiments, the volume of the aqueous solution ranges from 0.5-20 ml, from 1-15 ml, from 2-10 ml, from 3-8 ml, or from 5-6 ml. Preferably a volume of 10 ml aqueous solution is used.

In some embodiments, the aqueous solution in (a) has a pH of 4-12, 8-12, or preferably 9.5-11.5, or more preferably 10.5.

In some embodiments, the aqueous solution in (a) comprises 20-25%, or more preferably 23%, by weight/volume of sodium chloride. The presence of sodium chloride in the aqueous solution decreases the solubility of the extraction solvent in the aqueous phase. In the method, sodium chloride can be replaced by one or more other salts, which include sodium bisulfate ($NaHSO_4$), calcium chloride ($CaCl_2$), and salts of other alkali and alkaline earth metals, such as potassium and magnesium.

In some embodiments, the one or more N-nitrosamines present in the aqueous solution in (a) are not derivatized, i.e. the NAs in the aqueous solution are not chemically transformed into NA derivatives prior to be extracted by the disclosed method.

In some embodiments, the one or more N-nitrosamines are selected from the group consisting of N-nitroso-di-n-propylamine (NDPA), N-nitrosopiperidine (NPIP), N-nitroso-di-n-butylamine (NDBA), N-nitrosodiethylamine (NDEA), N-nitrosodimethylamine (NDMA), N-nitroso-di-n phenylamine (NDPhA), N-nitrosomethylethylamine (NMEA), N-nitrosomorpholine (NMOR), N-nitrosopyrrolidine (NPYR), and a combination thereof.

In one embodiment, the aqueous solution is preferably placed into a sample vial, which is preferably placed on an autosampler tray (e.g. Combi PAL) to perform the automated dispersive liquid-liquid microextraction technique to extract N-nitrosamines from the sample. The autosampler is used also when performing gas chromatography and mass spectrometry analysis. The autosampler, preferably a Combi PAL autosampler or the like, advantageously carries out the extracting, e.g. by agitating, and controls the extracting or agitating time and the extracting or agitating temperature, such as 5-40° C., 10-35° C., 15-30° C., or 20-25° C., in an automated fashion, minimizing human intervention and enhancing the extraction performance and the consistency in the N-nitrosamine detection and quantification results.

The extraction solvent of the disclosed method preferably has a low solubility in water or the aqueous solution, a capability of extracting N-nitrosamines from water or the aqueous solution, an efficient dispersibility, and a good chromatographic behavior. In some embodiments, the extraction solvent is less dense than water, and it may be at least one selected from the group consisting of cyclohexane, hexane, isooctane, n-pentane, toluene, p-xylene, a xylene isomers mixture, dibutyl ether, and mesitylene. When the extraction solvent is less dense than water, the organic phase in (b) is above the aqueous phase. In other embodiments, the extraction solvent is denser than water, and it may be at least one selected from the group consisting of chlorobenzene, carbon tetrachloride, carbon dichloride, chloroform, and tetrachloroethylene. When the extraction solvent is denser than water, the organic phase in (b) is below the aqueous phase.

The dispersive solvent of the disclosed method preferably has a good miscibility with both the extraction solvent and the aqueous solution. In some embodiments, the dispersive solvent is at least one selected from the group consisting of methanol, ethanol, acetonitrile, and acetone.

In one embodiment, prior to (a) extracting, the extraction solvent and the dispersive solvent are added to the aqueous solution together as a pre-formed mixture in an automated fashion. This is a preferred embodiment for an autosampler equipped with at least two syringes, one small volume syringe for GC injection and one large volume syringe for liquid transfer processes.

In another embodiment, prior to (a) extracting, the addition of the extraction solvent to the aqueous solution occurs prior to the addition of the dispersive solvent to the aqueous solution. In some embodiments, the addition of the extraction solvent to the aqueous solution is manual whereas the addition of the dispersive solvent to the aqueous solution is automated. This is a preferred embodiment for an autosampler equipped with only one small volume syringe. In this embodiment, the adjustment of the pH of the aqueous solution, the addition of the salt, e.g. NaCl, and the extraction solvent to the aqueous solution are done manually. The following steps, including the addition of the dispersive solvent, the extraction, and the GC-MS analysis, are fully automated.

In one embodiment, in (a) the extraction solvent comprises p-xylene and the dispersive solvent comprises methanol, and the volume ratio of the extraction solvent to the dispersive solvent ranges from 80:1 to 10:1, preferably from about 60:1 to 15:1, preferably from about 40:1 to 25:1, or more preferably about 30:1. At the preferred volume ratio of the extraction solvent to the dispersive solvent, the dispersive solvent facilitates the dispersion of the extraction solvent in the aqueous solution without decreasing the enrichment factor due to an increased solubility of the N-nitrosamines in the aqueous phase in (b).

The volume of the extraction solvent in the method may vary, depending on the ease of collection and volume measurement of the organic phase (to calculate the recovery rate), the enrichment factor (EF) and recovery rate desired, and evaporation of the extraction solvent. Generally, the EF decreases, whereas the recovery rate increases, with increasing volumes of the extraction solvent. In some embodiments, the volume of the extraction solvent is about 0.1-10 ml, about 0.3-8 ml, about 0.5-6 ml, about 0.7-4 ml, about 0.9-2 ml, or about 1 ml. In other embodiments, the volume ratio of the aqueous solution to the extraction solvent is about 20:1, about 15:1, about 10:1, about 5:1, about 3:1, or about 1:1.

The volume of the dispersive solvent may be adjusted accordingly based on the ratios of the extraction solvent to the dispersive solvent described above. Otherwise, at low volumes of the dispersive solvent, a cloudy state resulting from fine droplets of the extraction solvent dispersed in the aqueous solution is not formed well, and the extraction is not complete or efficient. On the other hand, at high volumes of the dispersive solvent, the solubility of the N-nitrosamines in the aqueous solution increases, reducing the extraction efficiency as well.

During the mixing in (a), the mixture of the extraction solvent, the dispersive solvent, and the aqueous solution is typically in a cloudy state resulting from the formation of fine droplets of the extraction solvent dispersed into the aqueous solution, with the one or more N-nitrosamines in the aqueous solution being extracted into the fine droplets of the extraction solvent. In some embodiments, at least 60%, preferably at least 70%, more preferably at least 80%, more preferably at least 90% of the one or more N-nitrosamines re-distribute from the aqueous solution to the extraction solvent. In other words, at least 60%, preferably at least 70%, more preferably at least 80%, more preferably at least 90% of the one or more N-nitrosamines are recovered by the extraction solvent from the aqueous solution.

In one embodiment, mixing the extraction solvent and the dispersive solvent with the aqueous solution in (a) comprises agitating the mixture of the extraction solvent, the dispersive solvent, and the aqueous solution using, for example, an agitator, a vortexer, or a shaker. In this embodiment, the extraction time is the duration of the agitation. In some embodiments, the speed of the agitating is between 500 and 750 rotations per minute, preferably between 700 and 750 rotations per minute, or more preferably 722 rotations per minute. In some embodiments, the duration of the agitating is between 15 and 50 minutes, preferably between 20 and 40 minutes, more preferably between 25 and 30 minutes, or more preferably about 28 minutes.

In another embodiment, mixing the extraction solvent and the dispersive solvent with the aqueous solution in (a) comprises sonicating the mixture of the extraction solvent, the dispersive solvent, and the aqueous solution using a sonicator. In this embodiment, the extraction time is the duration of the sonication. The sonicator used may be a probe sonicator inserted into the mixture, or more preferably a water bath sonicator that can sonicate a plurality of mixture samples without a direct contact between the sonicator and the mixture samples. Without such a direct contact, the chance of cross-sample contamination is reduced and cleaning of the sonicator between different samples is not needed. It is within the capability of a person skilled in the art to determine the sonication power setting and duration to obtain the desirable enrichment factor and recovery rate using the disclosed automated method. In some embodiments, the sonication duration is about 3-20 min, about 5-15 min, or about 8-12 min. The ultrasonic frequency is about 20-120 kHz, about 40-100 kHz, or about 60-90 kHz. In other embodiments, the sonicating results in at least 60%, preferably at least 70%, more preferably at least 80%, more preferably at least 90% of the one or more N-nitrosamines being recovered by the extraction solvent from the aqueous solution.

In one embodiment, the preferred extraction parameters for the automated dispersive liquid-liquid microextraction method of detecting and quantifying N-nitrosamines, such as the duration or time for the extracting, e.g. by agitating, the dispersive solvent volume, the pH of the aqueous solution, the sodium chloride concentration in the aqueous solution, the agitating speed, and the power level and time of sonication (if sonication is used for the extracting), are determined by response surface methodology, preferably with the aid of suitable computer software, such as Design Expert 8.0, its equivalent or like software. In statistics, response surface methodology (RSM) explores the relationships between several explanatory variables and one or more response variables. The main idea of RSM is to use a sequence of designed experiments to obtain a preferred response, or a preferred extraction parameter in the present disclosure. In a preferred embodiment, the preferred extraction parameters are applied in the disclosed method to determine the concentrations of N-nitrosamines in real water samples, such as tap water and ground water.

In one embodiment, permitting the resulting mixture in (a) to form a two-phase mixture comprises waiting for a sufficient period of time, e.g. at least 30 seconds, at least 1 minute, at least 3 minutes, at least 5 minutes, etc., for the complete formation of the organic and aqueous phases. In another embodiment, permitting the resulting mixture in (a) to form a two-phase mixture comprises centrifuging the resulting mixture in (a) for an effective period of time (e.g. at least 1 minute, at least 3 minutes, or at least 5 minutes, etc.), at an effective speed (e.g. 1000-6000 rpm, at 3000-5000 rpm, or at 4000 rpm). Once the formation of the aqueous phase and the organic phase is complete, the volume of the organic phase can be determined, for example, by using a syringe, a calibrated cylinder, or other liquid volume measuring devices well known in the art, for the calculation of the NA recovery rates.

In some embodiments, the organic phase is totally or substantially totally collected following (b), and then (a) is repeated followed by (b) again where a second organic phase is totally or substantially totally collected. This kind of (b)-(a)-(b) repetition may be performed once or more than once to increase the recovery rate of the NAs from the aqueous solution. Of course, each additional organic phase sample obtained from each repetition is subjected to (c) to determine the concentration of the NAs in the each additional organic phase.

In the method, the organic phase containing the extracted one or more N-nitrosamines, or a portion of the organic phase, is injected into an injection port of a gas chromatograph for separation followed by detection by a detector coupled with the gas chromatograph. In one embodiment, the detection and quantification of the concentration of the one or more N-nitrosamines in the aqueous solution is via the gas chromatography coupled with mass spectrometry that may comprise a single mass spectrometer (i.e. GC-MS) or a plurality of mass spectrometers, i.e., tandem mass spectrometry, such as GC-MS-MS. During the MS, the N-nitrosamines can be fragmented by either electron ionization, or preferably positive chemical ionization, for example, with methanol as the chemical ionization reagent. In other embodiments, the detection and quantification of the concentration of the one or more N-nitrosamines in the aqueous solution is via the gas chromatography coupled with a flame ionization detector (FID), a thermal energy detector, a nitrogen-phosphorus detector, or a nitrogen chemiluminescence detector.

Following the analysis, the enrichment factors (EFs) and the recovery rates can be calculated using Equations (I) and (II), respectively.

$$EF = C_{org}/C_0 \quad (I)$$

where EF, $C_{org}$, and $C_0$ are enrichment factor, concentration of N-nitrosamine in the organic phase, and initial concentration of N-nitrosamine in the aqueous solution, respectively.

$$R\% = (C_{org} \times V_{org}) \times 100/(C_0 \times V_{aq}) = (EF \times V_{org}) \times 100/V_{aq} \quad (II)$$

where R %, $V_{org}$, and $V_{aq}$ are recovery rate, volume of the organic phase, and volume of the aqueous solution, respectively. Calculation of $C_{org}$ was done by direct injection of N-nitrosamine standard solutions in the extraction solvent with concentrations in the linear range and comparison of the magnitudes of their detection signals, e.g. the peak areas of ion chromatograms from GC-MS, with those of the aqueous solution samples.

In some embodiments, the injecting produces a detection signal and the magnitude of the detection signal from the gas chromatography and mass spectrometry linearly correlates with the concentration of the one or more N-nitrosamines ranging from 0.01 to 1000 µg/L, from 0.02 to 800 µg/L, from 0.04 to 600 µg/L, from 0.06 to 400 µg/L, from 0.08 to 200 µg/L, or from 0.1 to 100 µg/L.

In some embodiments, the detection limit of the gas chromatograph and mass spectrometer for detecting the concentration of the one or more N-nitrosamines in the aqueous solution is between 1.0 and 500 ng/L, or between 2.5 and 400 ng/L, or between 3.5 and 300 ng/L, or between 4.0 and 250 ng/L, or between 5.0 and 124 ng/L, or between 5.7 and 52 ng/L.

Having generally described this invention, a further understanding can be obtained by reference to certain specific examples which are provided herein for purposes of illustration only and are not intended to be limiting unless otherwise specified.

Example 1

Materials and Methods
1. Chemicals

A mixture of NA standards was purchased from Sigma Aldrich (St. Louis, Mo., USA). It contained 2000 µg/L each of NDPA, NPIP, and NDBA. A stock solution of the three analytes was prepared in methanol (Merck, Darmstadt, Germany). A working standard solution was prepared daily with the appropriate dilution of the stock solution mixture. Doubly deionized water obtained from a Milli-Q system (Millipore, Bedford, Mass., USA) was used throughout the study. All solvents of analytical grade were purchased from Supelco (Bellefonte, Pa., USA). Sodium hydroxide, sulfuric acid, and sodium chloride were obtained from Merck. To avoid any contamination, all laboratory glassware was washed with concentrated hydrochloric acid and rinsed with deionized water and acetone, and dried out in a laboratory oven for 2 h at 100° C. before use.

2. Instrumentation

Analyses were performed on a GC-MS-QP 2010 supplied by Shimadzu (Kyoto, Japan) that was coupled to a CTC Analytics Combi PAL autosampler (Zwingen, Switzerland). FIG. 1 shows the number of steps involved in the entire DLLME procedure. Steps 4 to 17 were completely automated using the Combi PAL autosampler. A DB-5 fused-silica capillary column (30 m×0.25 mm id; 0.25 µm film thickness; J&W Scientific, Folsom, Calif., USA) was used for chromatographic separation. Ultra-high purity helium (99.999%, Abdulah Hashim, Al-Khobar, Saudi Arabia) was used as the carrier gas at a flow rate of 1.0 mL/min. Samples were injected in splitless mode. The sample volume used in the direct injection mode was 1 µL. The temperature program used for the analyses was as follows: the initial temperature of 40° C. was held for 3 min, which was then increased to 180° C. at 15° C. min$^{-1}$, and held for 2 min. The total run time was 14.5 min. The injection port, ion source, and interface temperatures were 200° C., 200° C., and 280° C., respectively. Full-scan mode with m/z values from 50 to 500, and selective ion monitoring mode were used for the MS analysis. The following ion sets were monitored: m/z 130, 84, 86 for NDPA; m/z 114, 84, 86 for NPIP; and m/z 84, 57,121 for NDBA.

3. Sample Preparation

To determine the extraction parameters, a 10 mL water sample (adjusted to a pH of 10.5) to which 2.3 g of sodium chloride (NaCl) and 1 mL of extraction solvent (p-xylene) were added was prepared in a sample vial manually and was then placed on the autosampler tray for DLLME. Dispersive solvent (methanol, 33 µL) and 90 µg/L of NAs were added automatically by using the autosampler syringe (of 10 µL capacity), the manipulation of which was preprogrammed. The vial was then conveyed to an agitator, and agitated at 722 rpm for 28 min. After a cloudy solution was formed, the vial was transported back to the autosampler tray, where it remained for 1 min. The cloudiness disappeared over this period. Then 1 µL of the upper layer of the solution, i.e. the organic phase, was retrieved automatically using the autosampler syringe and injected into the GC-MS for analysis. FIG. 1 shows the entire automated procedure handled by the autosampler.

4. Calculation of Enrichment Factor

The enrichment factor is defined as the ratio of the analyte concentration in the organic phase ($C_{org}$) and the initial concentration of the analyte in the standard sample ($C_0$), according to Equation (1):

$$EF = C_{org}/C_0 \quad (1)$$

$C_{org}$ is obtained from a calibration graph prepared by direct injection of an NA standard solution made with the extraction solvent.

5. Experimental Design

Response surface methodology (RSM), a multi-variant statistical modeling technique, was used to evaluate the effects of the independent variables and their interactions on the EF and also to establish the automated DLLME technique. RSM, which involves designing experiments according to factorial design, enables development of quartic polynomial models and response surfaces. The RSM process is very economical as it only requires a small number of experimental runs compared to one variable at a time approaches. With the automation enabled in the present disclosure, the convenience of executing the experiments is even more pronounced, now that a reduced number of experiments needed to be conducted automatically. In addition, the design is also suited for curvature (i.e. non-linear behaviors of response surface) in the response function, which cannot be achieved in first-order design methods.

Using the RSM, the effects of different parameters (A, extraction time; B, volume of dispersive solvent, C, water sample pH; D, NaCl concentration; E, agitation speed) were investigated to determine their respective influences. The interactions among the parameters on the DLLME EFs and limits of detection (LODs) for the three NAs (i.e. NDPA, NPIP, and NDBA) were determined. A Box-Behnken design (BBD) was employed for developing polynomial models with the aid of statistical software, Design Expert 8.0 (Stat-Ease, Minneapolis, Minn., USA). As the BBD experimental design is an orthogonal design, factor levels are evenly spaced and coded for low, medium (central point), and high level, as −1, 0, and +1, respectively, calculated according to Equation (2) and shown in Table 1. A total of 41 experimental runs were needed for implementing the BBD for the present disclosure. Table 2 shows the extraction parameter settings and the average EFs for the individual NAs, i.e. NDPA, NPIP, and NDBA, and the total NAs of the 41 experimental runs. Each of the 41 runs was repeated three times and their average was used to determine the relative standard deviations (RSDs).

$$xi = \frac{Xi - (Xhigh + X\ low)/2}{(X\ high - Xlow)/2} \quad (2)$$

where $x_i$ is the coded value and $X_i$ is the original value.

TABLE 1

Actual and coded values of five variables in Design Expert

| | | | Coded and actual level | | |
|---|---|---|---|---|---|
| Variable | Component | Unit | −1 | 0 | +1 |
| A | Extraction time | min | 10 | 20 | 30 |
| B | Dispersive solvent volume | µL | 15 | 30 | 45 |
| C | Water sample pH | — | 4 | 8 | 12 |
| D | NaCl concentration | % (w/v) | 0 | 15 | 30 |
| E | Agitation speed | rpm | 250 | 500 | 750 |

TABLE 2

Experimental conditions for determining the values for the following variables: A, extraction time; B, volume of dispersive solvent; C, water sample pH; D, NaCl concentration; E, agitation speed

| | Independent Variable | | | | | Average of enrichment factor (n = 3) | | | |
|---|---|---|---|---|---|---|---|---|---|
| Exp. | A (min) | B (µL) | C | D (%) | E (rpm) | NDPA | NPIP | NDBA | Total nitrosoamine |
| 1 | 30 | 45 | 8 | 15 | 500 | 50.80 | 25.07 | 40.42 | 116.29 |
| 2 | 30 | 30 | 12 | 15 | 500 | 42.78 | 22.22 | 43.91 | 108.9 |
| 3 | 20 | 30 | 8 | 0 | 750 | 41.20 | 16.46 | 41.74 | 99.4 |
| 4 | 20 | 45 | 8 | 30 | 500 | 32.52 | 16.09 | 19.92 | 68.53 |
| 5 | 10 | 30 | 4 | 15 | 500 | 28.12 | 17.57 | 23.70 | 69.4 |
| 6 | 10 | 30 | 8 | 0 | 500 | 34.98 | 15.56 | 35.98 | 86.51 |
| 7 | 20 | 30 | 8 | 0 | 250 | 53.16 | 13.62 | 31.30 | 98.09 |
| 8 | 30 | 30 | 8 | 30 | 500 | 36.29 | 21.38 | 37.44 | 95.11 |
| 9 | 20 | 15 | 8 | 0 | 500 | 36.48 | 15.48 | 36.12 | 88.08 |
| 10 | 30 | 15 | 8 | 15 | 500 | 28.90 | 10.78 | 19.11 | 58.8 |
| 11 | 10 | 30 | 8 | 15 | 250 | 23.14 | 10.72 | 14.13 | 47.99 |

TABLE 2-continued

Experimental conditions for determining the values for the following variables: A, extraction time; B, volume of dispersive solvent; C, water sample pH; D, NaCl concentration; E, agitation speed

| | Independent Variable | | | | | Average of enrichment factor (n = 3) | | | |
|---|---|---|---|---|---|---|---|---|---|
| Exp. | A (min) | B (µL) | C | D (%) | E (rpm) | NDPA | NPIP | NDBA | Total nitrosoamine |
| 12 | 30 | 30 | 8 | 15 | 750 | 44.50 | 23.46 | 52.47 | 120.43 |
| 13 | 20 | 30 | 4 | 15 | 750 | 37.10 | 21.65 | 34.42 | 93.17 |
| 14 | 20 | 45 | 8 | 15 | 250 | 22.79 | 19.09 | 9.20 | 51.09 |
| 15 | 20 | 30 | 4 | 15 | 250 | 25.04 | 18.32 | 14.03 | 57.39 |
| 16 | 10 | 45 | 8 | 15 | 500 | 35.67 | 17.60 | 23.36 | 76.62 |
| 17 | 20 | 15 | 8 | 15 | 250 | 27.75 | 17.32 | 17.07 | 62.14 |
| 18 | 20 | 30 | 8 | 15 | 500 | 33.96 | 13.94 | 29.02 | 76.91 |
| 19 | 10 | 30 | 8 | 30 | 500 | 27.52 | 17.84 | 18.23 | 63.59 |
| 20 | 20 | 30 | 12 | 15 | 250 | 25.47 | 15.79 | 14.44 | 55.7 |
| 21 | 20 | 45 | 8 | 15 | 750 | 36.66 | 18.66 | 31.39 | 86.71 |
| 22 | 20 | 30 | 8 | 30 | 750 | 46.34 | 29.35 | 44.73 | 120.42 |
| 23 | 20 | 30 | 8 | 30 | 250 | 12.34 | 20.89 | 10.35 | 43.58 |
| 24 | 10 | 30 | 12 | 15 | 500 | 22.90 | 14.10 | 14.80 | 51.81 |
| 25 | 20 | 45 | 4 | 15 | 500 | 34.31 | 17.86 | 19.17 | 71.34 |
| 26 | 20 | 15 | 12 | 15 | 500 | 45.32 | 24.36 | 43.19 | 112.87 |
| 27 | 20 | 15 | 8 | 30 | 500 | 15.96 | 10.71 | 13.85 | 40.52 |
| 28 | 20 | 30 | 12 | 0 | 500 | 22.51 | 10.88 | 16.31 | 49.71 |
| 29 | 20 | 30 | 12 | 15 | 750 | 45.86 | 23.10 | 40.65 | 109.61 |
| 30 | 20 | 30 | 4 | 30 | 500 | 39.82 | 29.93 | 36.67 | 106.43 |
| 31 | 30 | 30 | 8 | 15 | 250 | 27.95 | 21.37 | 24.61 | 73.93 |
| 32 | 20 | 15 | 8 | 15 | 750 | 23.55 | 6.62 | 13.50 | 43.67 |
| 33 | 10 | 15 | 8 | 15 | 500 | 28.41 | 19.14 | 20.98 | 68.53 |
| 34 | 10 | 30 | 8 | 15 | 750 | 39.28 | 21.39 | 42.38 | 103.05 |
| 35 | 30 | 30 | 8 | 0 | 500 | 34.46 | 13.25 | 31.96 | 79.67 |
| 36 | 20 | 45 | 8 | 0 | 500 | 32.42 | 14.92 | 33.42 | 80.75 |
| 37 | 30 | 30 | 4 | 15 | 500 | 34.85 | 17.80 | 30.03 | 82.68 |
| 38 | 20 | 30 | 4 | 0 | 500 | 27.58 | 13.15 | 27.96 | 68.69 |
| 39 | 20 | 30 | 12 | 30 | 500 | 35.46 | 28.52 | 45.06 | 109.04 |
| 40 | 20 | 45 | 12 | 15 | 500 | 39.37 | 20.41 | 40.13 | 99.9 |
| 41 | 20 | 15 | 4 | 15 | 500 | 40.18 | 20.47 | 37.00 | 97.65 |

The experimental run sequences were randomized to eliminate the effects of the uncontrolled factors to ensure data quality.

The behavior of the mathematical response models was generally represented by the polynomial function in Equation (3) for quartic behavior.

$$\gamma = \beta_o + \sum_{i=1}^{k} \beta_i x_i + \sum_{i=1}^{k} \beta_{ii} x_i^2 + \sum_{i=1}^{k-1}\sum_{j=2}^{k} \beta_{ij} x_i x_i + \dots + \varepsilon \quad (3)$$

where $\gamma$ is the predicted response, $\beta_0$ the constant coefficient, $\beta i$ the linear terms coefficients, $\beta ij$ the interaction terms coefficients, $\beta ii$ the quartic terms coefficients, and $x_i$, $x_j$ the coded values of the independent variables, and c the error.

Example 2

Selection of a Preferred Combination of the Extraction Solvent and the Dispersive Solvent for the Automated Dispersive Liquid-Liquid Microextraction Method of Detecting and Quantifying N-Nitrosamines There are specific criteria for choosing the preferred extraction solvent, such as: (i) density (lower or higher than that of water; the former type is generally considered more environment friendly), (ii) low solubility in water, (iii) the capability of extracting analytes from an aqueous sample, (iv) efficient dispersibility of the solvent, and (v) good chromatographic behavior. One main criterion of a suitable dispersive solvent is its miscibility with both the extraction solvent and aqueous sample. Hexane, isooctane, n-pentane, toluene, and p-xylene were chosen as candidate extraction solvents, and methanol, acetonitrile, and acetone were chosen as candidate dispersive solvents. The combination of p-xylene/methanol was determined to display a satisfactory performance in the automated DLLME of N-nitrosamines with respect to, for example, providing high enrichment factors and high recovery rates for the N-nitrosamines.

Example 3

Determination of Extraction Parameters for the Automated Dispersive Liquid-Liquid Microextraction Method of Detecting and Quantifying N-Nitrosamines Using Response Surface Methodology (RSM)

Using response surface methodology (RSM), 3D response surface curves and their corresponding contour maps for the EF models were constructed, with the independent variables of (A) extraction time, (B) dispersive solvent volume, (C) water sample pH, (D) sodium chloride concentration, and (E) agitation (stirring) speed and their relative interactions on the EFs. Each of the response curves shown in FIGS. 2, 3, and 4 was developed by fixing three of the independent variables while varying the remaining two within the investigated ranges. These curves corroborate the analysis of variance (ANOVA) analysis shown in Table 3, revealing that all the independent variables had significant contributions to the responses. Both depict the effects of all the variables on the extraction of NAs, showing that the EFs were affected by all the investigated variables (A-E).

TABLE 3

ANOVA for the quartic order regression model obtained from experimental data

| | $EF_{NDBA}$ ($R^2 = 0.999$) | | $EF_{NPIP}$ ($R^2 = 0.877$) | | $EF_{NDPA}$ ($R^2 = 0.833$) | |
|---|---|---|---|---|---|---|
| | Precision | | | | | |
| | 9.7 | | 8.59 | | 7.26 | |
| | F-value | p-value[a] | F-value | p-value[a] | F-value | p-value[a] |
| Model | 432.02 | 0.0023* | 4.3 | 0.0025* | 3.69 | 0.0039* |
| A | 209.59 | 0.0047* | 3.24 | 0.0922** | 8.67 | 0.0091* |
| B | 83.42 | 0.0118* | 4.35 | 0.0546** | 0.3 | 0.5886 |
| C | 105.91 | 0.0093* | 0.05 | 0.8288 | 1.46 | 0.2429 |
| D | 39.68 | 0.0243* | 13.19 | 0.0025* | 6.75 | 0.0188* |
| E | 2660.3 | 0.0004* | 11.33 | 0.0042* | 33.73 | 0.0001* |

Figure 2:
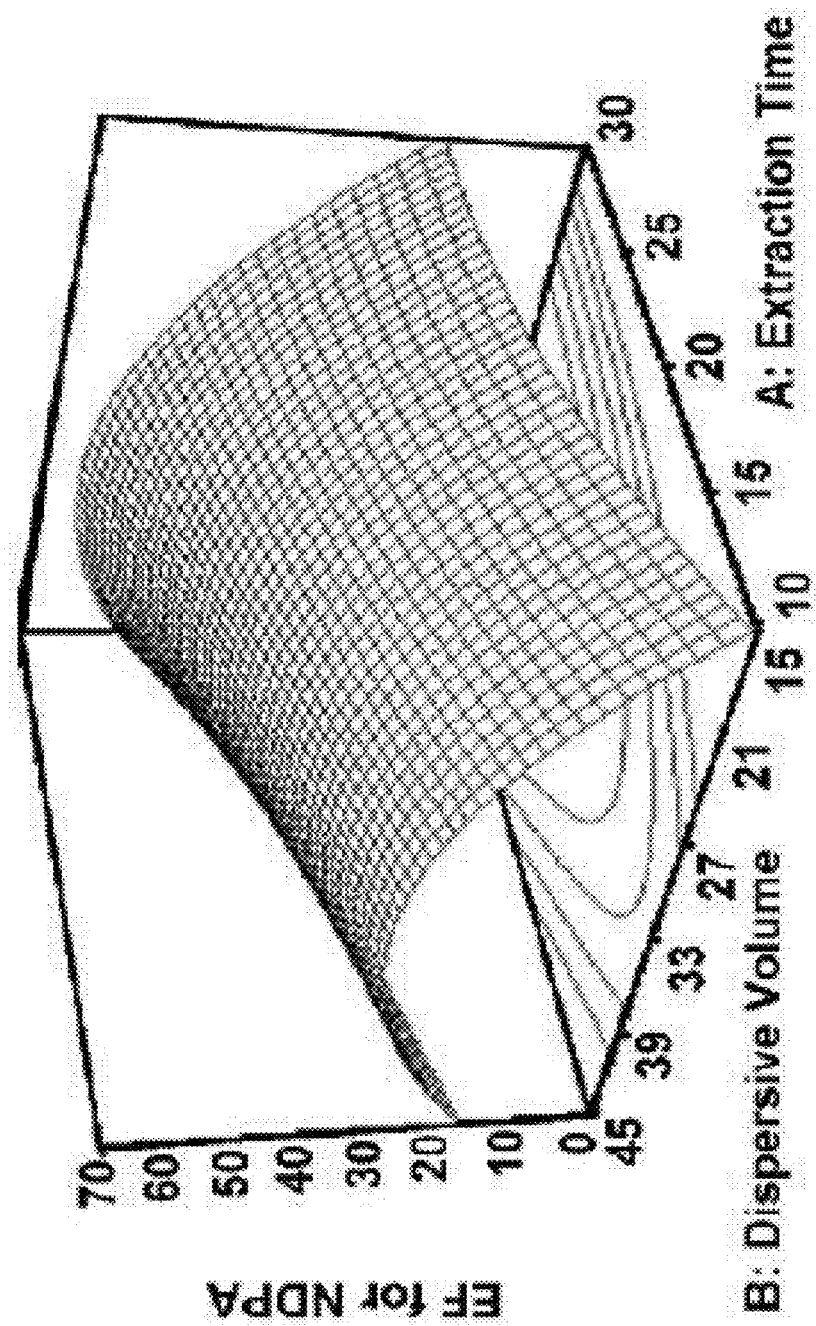
FIG. 2 is a graphical presentation of the response surface curve showing the effects of the extraction time (A) and dispersive solvent volume (B) on DLLME of NDPA from water samples with the water sample pH of 12, the NaCl concentration of 23% (w/v), and the agitation speed of 750 rpm.
Figure 3:
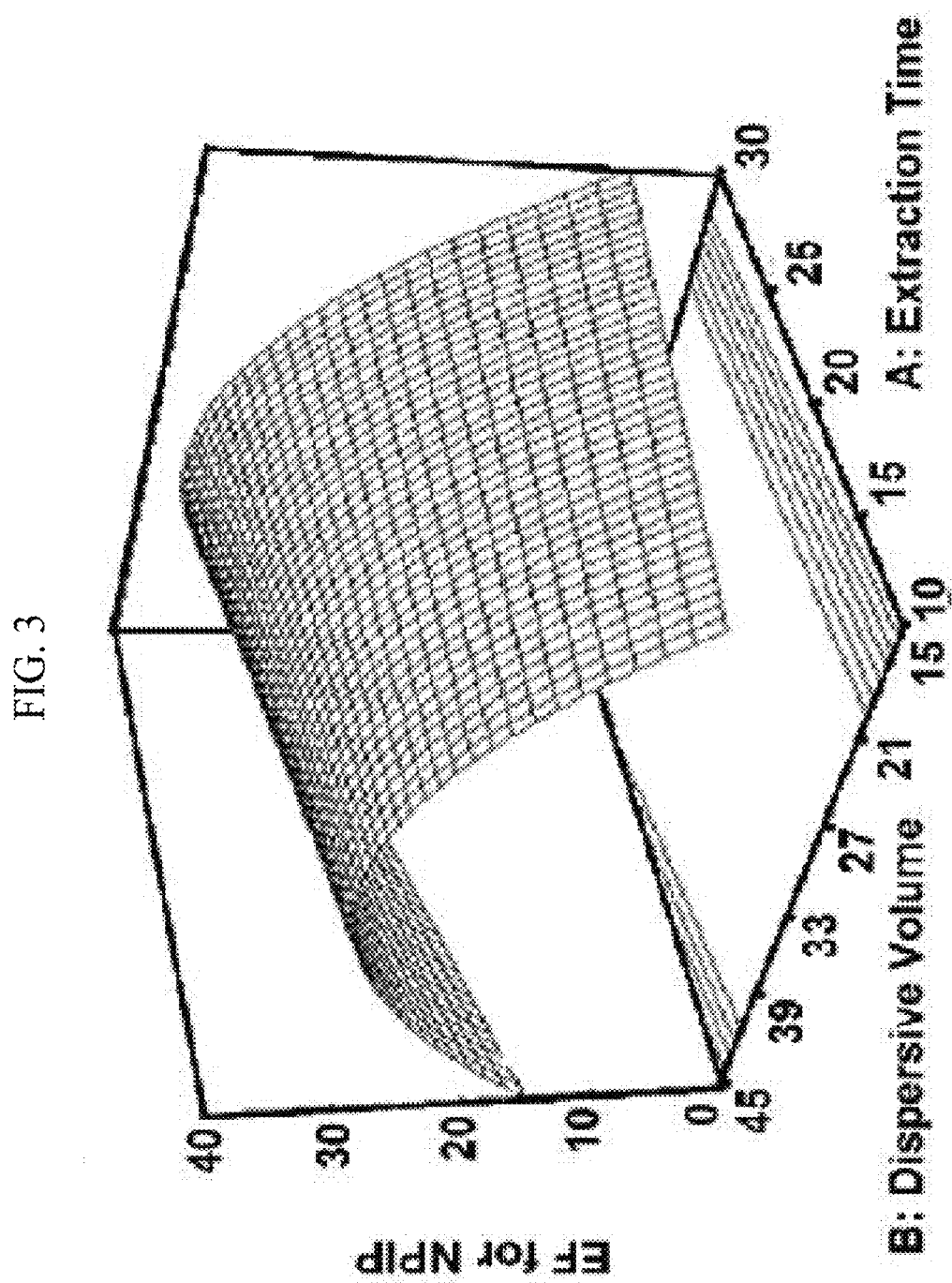
FIG. 3 is a graphical presentation of the response surface curve showing the effects of the extraction time (A) and dispersive solvent volume (B) on DLLME of NPIP from water samples with the water sample pH of 12, the NaCl concentration of 23% (w/v), and the agitation speed of 750 rpm.
Figure 4:
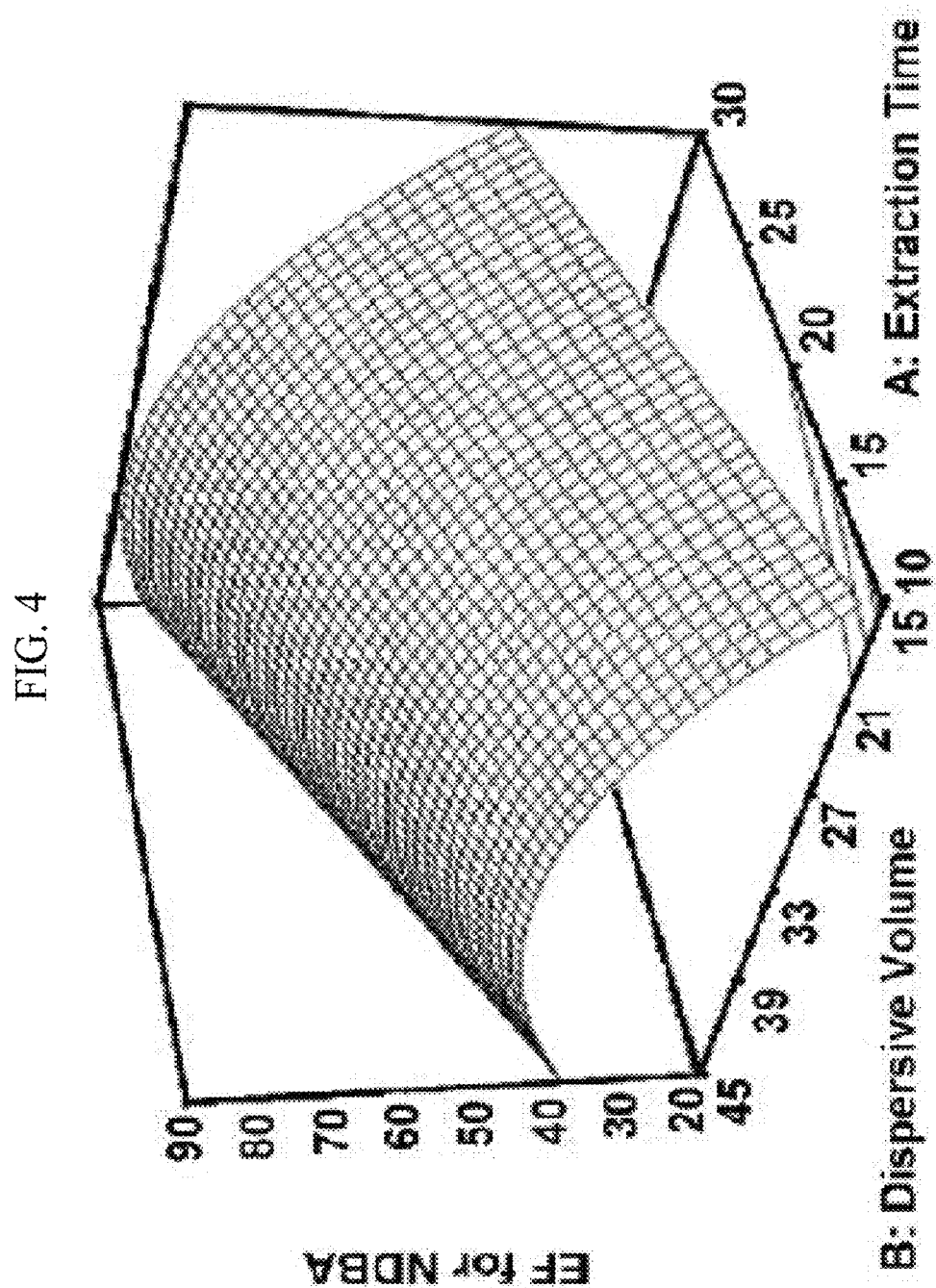
FIG. 4 is a graphical presentation of the response surface curve showing the effects of the extraction time (A) and dispersive solvent volume (B) on DLLME of NDBA from water samples with the water sample pH of 12, the NaCl concentration of 23% (w/v), and the agitation speed of 750 rpm.

[a](*) Significance was established at $p < 0.05$ and () Significance was established at $p < 0.01$ The dependence of the EFs for the extraction of NDPA, NPIP, and NDBA on the extraction time (A) and the dispersive solvent volume (B) at fixed values of the water sample pH of 12, the NaCl concentration of 30%, and the agitation speed of 750 rpm is depicted in FIG. 2, FIG. 3, and FIG. 4**, respectively. The response curves indicated the general trends of a linear increase in the extraction efficiencies represented by the EFs with the increasing extraction time (A) regardless of the volume of the dispersive solvent selected within the test range. By contrast, varying the dispersive solvent volume (B) while maintaining the same extraction time gave rise to the response surface curves that showed an initial increase in the EFs with the increasing dispersive solvent volume (B). The increase in the EFs reached a plateau when the dispersive solvent volume was around 354 followed by a decline in the EFs with a further increase in the dispersive solvent volume up to the maximum volume tested. The EFs were low at the low volumes of the dispersive solvent (methanol) due to the difficulty of the extraction mixture reaching a cloudy state. At the high volumes of the dispersive solvent, the solubility of the NAs in the aqueous phase increased, leading to a decrease in the EFs. In a conventional DLLME experiment conducted manually, a mixture of dispersive and extraction solvents is rapidly injected into an aqueous sample. Since the autosampler used in the present disclosure was a one-syringe model, and since the expulsion of liquids from the syringe could not be done rapidly, to generate a cloudy solution, agitation of the sample was chosen as an alternative. Since the extraction, including the agitation, was fully automated, the 28 min preferred extraction, or agitation, time for the disclosed automated DLLME method may be advantageously scheduled and run outside of office hours.

At the fixed high level values for the water sample pH of 12, the NaCl concentration of 30%, and the dispersive solvent volume of 45 μL, the combined influence of the agitation speed (E) and the extraction time (A) further corroborated the linear positive effect of the extraction time on the extraction efficiencies for all the NAs. The marked increase in the EFs with the increasing extraction time and agitation speed resulted in the maximum EF for NPIP being achieved at the mid-level of the agitation speed, i.e. 500 rpm. A further increase in the agitation speed resulted in a decrease in the EF. The decrease in the extraction efficiency with a further increased agitation speed could be attributed to back extraction that is more likely to take place at high agitation speeds. While high EF values of about 60 and 90 were achievable for NDPA and NDBA, respectively, as shown in FIG. 2 and FIG. 4, the EF value for NPIP was much lower, of about 35, as shown in FIG. 3. Generally speaking, increasing the agitation speed (to a level before any back extraction occurs) and extraction time has a positive effect on the extraction efficiencies for the NAs.

The relative effect of the agitation speed (E) and the dispersive solvent volume (B) was also studied. The response surface curves showed that the highest EF values for the three NAs were located inside the experimental range around the central values of E and B. Similarly, the interaction between the water sample pH (C) and the NaCl concentration (D) showed similar trends for NDPA and NPIP extraction based on the response curves, which indicated a fairly linear increase in the EFs for all the NAs with increasing NaCl concentrations. Changing the pH affected only slightly the EFs for NDPA and NPIP. On the other hand, the sample pH had a stronger effect on the EF for NDBA, as indicated by a more pronounced curvature of the response surface with the water sample pH as a variable. This could be due to a stronger hydrolysis of NDBA that takes place at a high pH compared to that of NDPA and NPIP. Additionally, higher EF values were achieved for NDPA and NDBA than for NPIP. Thus, among the three NAs investigated, NPIP was extracted from the water sample least efficiently using the automated DLLME technique. Further, in contrast to the extraction time (A), each of the other extraction parameters B, C, D, and E affected the EFs of the NAs in a non-linear fashion, with varying B (the dispersive solvent volume) resulting in a response surface with the strongest degree of curvature. Varying E (the agitation speed) resulted in a response surface with the second strongest degree of curvature. Varying C (the water sample pH) resulted in a response surface with the third strongest degree of curvature. Varying D (the NaCl concentration) resulted in a response surface with the least degree of curvature.

The conditions for the extraction of NDBA, NDPA and NPIP, and the EFs of the total NAs were predicted using the coded values of the independent variables. With the least parameters (i.e., 3) under investigation, finding a useful region through visual inspection of the response surfaces is possible in the absence of constraints. However, for a higher number of parameters (as in the case of the present disclosure), obtaining the global (rather than local) operating points within the experimental variable ranges was more challenging. As such, numerical simultaneous extraction of the NAs using DLLME was performed with the aid of Design-Expert® 8.0 software. The coordinates of the points were calculated through equating the first derivatives of the reduced models to zero according to Equation (4) in conjunction with a set of convergent criteria (Llop, A, Borrull, F., Pocurull, E., J. Sep. Sci. 2010, 33, 3692-3700, incorporated herein by reference in its entirety). The convergent criterion is composed of a set of goals based on desired constraints for the parameters of interest (responses and the independent variables). The criteria also weighted the individual parameters according to their relative importance in contributing to the attainment of the desired overall targeted goals.

$$\frac{\partial \gamma}{\partial x_i} = \beta_i + 2\beta_{ii} x_i + \sum_{j=2}^{k} \beta_{ij} x_i + \ldots = 0 \quad (4)$$

FIG. 2, FIG. 3, and FIG. 4 show examples of the numerical solutions that met the convergent criteria for maximizing the EFs for the three NAs with the highest desirability. The average of these solutions indicated that the conditions for simultaneous extraction of the NAs in a water sample were: the extraction time of 28 min, the dispersive solvent (methanol) volume of 33 µL, the agitation speed of 722 rpm, the NaCl concentration of 23% w/v, and the water sample pH of 10.5. Table 4 shows the EFs of the individual NAs, RSDs, and desirability obtained from an automated DLLME run with a set of triplicate samples under the operating conditions.

the extraction sequence was begun. With a dual-syringe autosampler, both the GC injection and the liquid transfer processes can be performed automatically by using a small-volume syringe and a large-volume syringe, respectively.

Example 4

Determination of the Analytical Performance of the Automated DLLME Method

To evaluate the disclosed method, the linear range, repeatability, and limits of detection (LODs) were investigated

TABLE 4

Numerical results for the NA extraction conditions using automated DLLME-GC-MS

| Samples | Variables | | | | | EF | | | | |
|---|---|---|---|---|---|---|---|---|---|---|
| | A | B | C | D | E | NDPA | NPIP | NDBA | % RSDs | Desirability |
| 1 | 28 | 33 | 10.5 | 22.95 | 722.29 | 41.75 | 27.1 | 56.73 | 1.47 | 0.89 |
| 2 | 28 | 33 | 10.5 | 22.93 | 721.85 | 41.74 | 27.11 | 56.73 | 1.47 | 0.89 |
| 3 | 28 | 33 | 10.5 | 22.97 | 722.05 | 41.77 | 27.08 | 56.79 | 1.47 | 0.89 |
| Average | 28 | 33 | 11 | 23 | 722 | 42 | 27 | 57 | 1.5 | 0.9 |

In a conventional manually operated DLLME experiment, a mixture of dispersive and extraction solvents is injected rapidly into a water sample. Since the autosampler used in the examples of the present disclosure was a single-syringe model, it was more convenient to separate the introduction of the solvents. Moreover, with a single syringe, a compromise had to be made between a good GC performance that prefers a small volume syringe for extract injection and a smaller number of liquid transfers that prefer a large volume syringe. To ensure a good GC performance, a small syringe was selected for the autosampler. As a result, following the manual adjustment of the pH of the water samples and manual addition of NaCl to the water samples, the extraction solvent p-xylene was preloaded to the water samples also manually. Since the subsequent extraction procedure was fully automated, no further human effort was needed once with the derived extraction parameters. Linearity was observed over the concentration range of 0.1-100 µg/L for the NAs and with coefficients of determination ($R^2$) ranging from 0.988 to 0.998. The repeatability study was carried out by extracting NA-spiked water samples containing 0.1, 0.5, 1, 10, 20, 37, 74, and 100 µg/L of the NAs, and the % RSDs were determined to be between 3.4 and 5.9% (n=4). The LODs, based on the signal to noise ratio of 3, ranged from 5.7 to 52 ng/L. The performance of the automated DLLME-GC-MS method was compared with that of other methods reported in the literature. The results are shown in Table 5. The data demonstrate that the performance of the automated DLLME-GC-MS method is comparable to that of the other methods reported, with the advantage of the complete automation from the extraction process to the GC-MS analysis.

TABLE 5

Comparison of the automated DLLME-GC-MS with other reported methods for the determination of NAs in water samples

| Method | Sample | Linear Range (ng/L) | LOD (ng/L) | RSDs (%) | Recovery Rates (%) | Ref |
|---|---|---|---|---|---|---|
| SPE-GC-EI-MS-MS[a] | Water | 500-50,000 | 0.4-4 | Max 10 | 82-102 | [1] |
| HS-SPME/GC-MS-MS[b] | Water | 10-1,500 | 1-5 | 3-13.0 | — | [2] |
| SPE-GC-FID[c] | Water | 10,000-600,000 | 2000-3500 | 3-6.5 | — | [3] |
| SPE-GC-NPD[d] | Water | 300-20,000 | 20-80 | 3.5-6.3 | 95-103 | [3] |
| SPE-GC-MS | Water | 40-20,000 | 3-13.0 | 4.1-6.1 | 95-103 | [3] |
| HPLC-CL[e] | Water | 5-1,000 | 1.5-3 | 0.7-4.5 | 94.8-102.8 | [4] |
| DLLME-GC-MS | Water | 100-100,000 | 5.7-52 | 3.4-5.9 | 90.3-112 | Present disclosure |

Recovery Rates were calculated using NA-spiked real water samples
[a]SPE GC with electron ionization MS/MS.
[b]Headspace solid-phase microextraction followed by GC MS/MS.
[c]SPE by GC with flame ionization detection.
[d]SPE by GC with nitrogen phosphorus detection.
[e]HPLC with chemiluminescence detection.
Refs:
[1] Grebel, J. E., Young, C. C., Suffet, I. H. M., J. Chromatogr. A 2006, 1117, 11-18.
[2] Kodamatani, H., Yamazaki, S., Saito, K., Amponsaa-Karikari, A, Kishikawa, N., Kurodad, N., Tomiyasu, T., Komatsu, Y., J. Chromatogr. A 2009, 1216, 92-98.
[3] Campillo, N., Vinas, P., Ferez-Melgarejo, G., Hernandez-Cordoba, M., J. Chromatogr. A 2013, 1282, 20-26.
[4] Anderson, M. J., Whitcomb, P. J., RSM Simplified: Optimizing Processes Using Response Surface Methods for Design of Experiments, Productivity Press, New York 2005.

Example 5

Detection and Quantification of NAs in Real Water Samples

Figure 5:
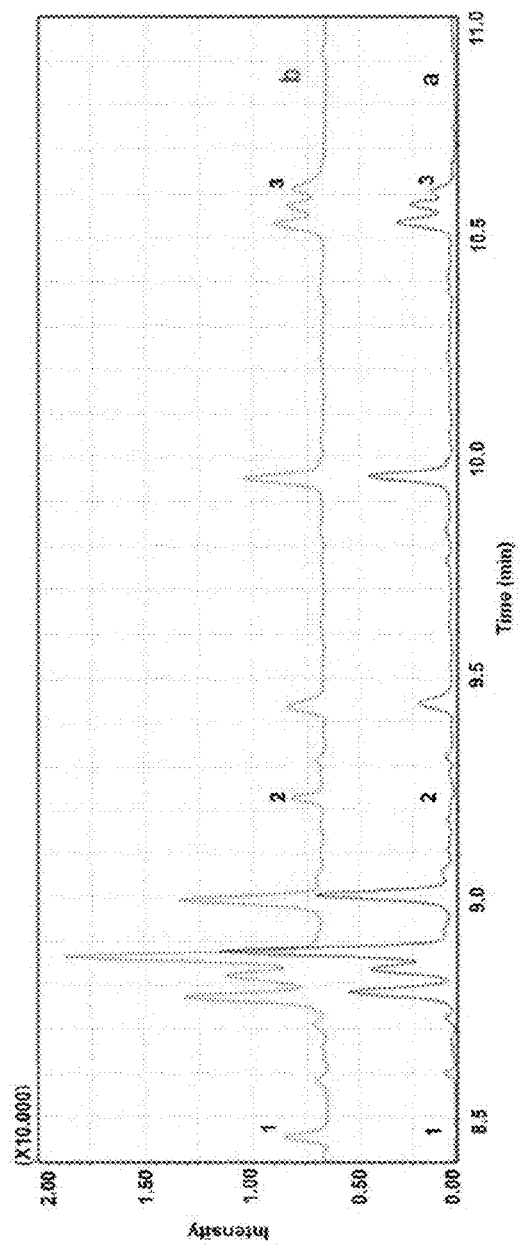
FIG. 5 is a graphical presentation of the total ion chromatograms, with (a) representing the total ion chromatogram of an unspiked raw groundwater sample and (b) representing the total ion chromatogram of a groundwater sample spiked with 2 µg/L of NDPA giving rise to Peak 1, NPIP giving rise to Peak 2, and NDBA giving rise to Peak 3.

The automated DLLME-GC-MS method was applied to determine the NAs in different types of water samples: tap water, and groundwater before and after treatment in a water purification plant in the main campus of King Fand University of Petroleum and Minerals (KFUPM), Saudi Arabia. Ten millimeters of each sample were used for the automated DLLME method. Referring to FIG. 5, total ion chromatogram (a), only NDBA represented by Peak 3 was detected in raw groundwater samples. NDPA and NPIP were not detected in any of the samples. To assess the matrix effects that may affect the performance of the disclosed DLLME-GC-MS method, these real water samples were spiked with 2 µg/L each of the target analytes, i.e. NDPA, NPIP, and NDBA, and the recovery rates were calculated. The recovery rates of N-nitroso-di-n-propylamine (NDPA), N-nitrosopiperidine (NPIP), and N-nitroso-di-n-butylamine (NDBA) from the NA-spiked groundwater and tap water samples at concentrations of 2 µg/L of each analyte (expressed in mean±standard deviation, n=3) were (93.9±8.7)%, (90.6±10.7)%, and (103.7±8.0)%, respectively. Referring to FIG. 5, total ion chromatogram (b), peaks 1, 2, and 3 indicate the presence of the spiked NDPA, NPIP, and NDBA, respectively. Thus, the recovery rates for the NAs in groundwater and tap water samples ranged from 90.3% to 112.1%. Further, the disclosed method is suitable for different real water samples with no significant matrix effects observed.

The invention claimed is:

1. An automated dispersive liquid-liquid microextraction method of detecting and quantifying one or more N-nitrosamines, comprising:
   (a) extracting an aqueous solution comprising the one or more N-nitrosamines by mixing an extraction solvent and a dispersive solvent with the aqueous solution, wherein the aqueous solution is contained in a sample container, wherein the one or more N-nitrosamines, or a portion thereof, re-distribute from the aqueous solution to the extraction solvent, wherein the mixing comprises sonicating the sample container containing the extraction solvent, the dispersive solvent, and the aqueous solution in a water bath,
   (b) permitting the resulting mixture in (a) to form a two-phase mixture comprising an aqueous phase comprising the aqueous solution with reduced amounts of the one or more N-nitrosamines and an organic phase comprising the extraction solvent with the one or more N-nitrosamines extracted from the aqueous solution,
   (c) injecting the organic phase, or a portion thereof, into an injection port of a gas chromatograph coupled with at least one mass spectrometer, and
   (d) analyzing the one or more N-nitrosamines by gas chromatography and mass spectrometry to detect and quantify the concentration of the one or more N-nitrosamines in the aqueous solution,
   wherein a volume ratio of the extraction solvent to the dispersive solvent is in a range of 80:1 to 10:1.

2. The method of claim 1, wherein the aqueous solution in (a) comprises at least one selected from the group consisting of tap water, well water, ground water, river water, waste water, and water treated with chlorine and/or ozone.

3. The method of claim 1, wherein the aqueous solution in (a) has a pH between 9.5 and 12.

4. The method of claim 1, wherein the aqueous solution in (a) comprises about 20-25% by weight/volume of sodium chloride.

5. The method of claim 1, wherein the one or more N-nitrosamines present in the aqueous solution in (a) are not derivatized.

6. The method of claim 1, wherein the one or more N-nitrosamines are selected from the group consisting of N-nitroso-di-N-propylamine (NDPA), N-nitrosopiperidine (NPIP), N-nitroso-di-N-butylamine (NDBA), N-nitrosodiethylamine (NDEA), N-nitrosodimethylamine (NDMA), N-nitroso-di-N-phenylamine (NDPhA), N-nitrosomethylethyl amine (NMEA), N-nitrosomorpholine (NMOR), N-nitrosopyrrolidine (NPYR), and a combination thereof.

7. The method of claim 1, wherein (a) the extraction solvent and the dispersive solvent are added to the aqueous solution together as a pre-formed mixture in an automated fashion.

8. The method of claim 1, wherein (a) the addition of the extraction solvent to the aqueous solution occurs prior to the addition of the dispersive solvent to the aqueous solution.

9. The method of claim 8, wherein (a) the addition of the extraction solvent to the aqueous solution is manual whereas the addition of the dispersive solvent to the aqueous solution is automated.

10. The method of claim 1, wherein the extraction solvent is at least one selected from the group consisting of cyclohexane, hexane, isooctane, N-pentane, toluene, p-xylene, a xylene isomers mixture, dibutyl ether, and mesitylene.

11. The method of claim 1, wherein the dispersive solvent is at least one selected from the group consisting of methanol, ethanol, acetonitrile, and acetone.

12. The method of claim 1, wherein (a) the extraction solvent comprises p-xylene and the dispersive solvent comprises methanol.

13. The method of claim 1, wherein the sonicating occurs at an ultrasonic frequency in a range of 20-120 kHz and for a period in a range of 3-20 minutes.

14. The method of claim 1, wherein (a) at least about 90% of the one or more N-nitrosamines re-distribute from the aqueous solution to the extraction solvent during the extracting.

15. The method of claim 1, wherein the injecting produces a detection signal and the magnitude of the detection signal from the gas chromatography and mass spectrometry linearly correlates with the concentration of the one or more N-nitrosamines ranging from 0.1 to 100 µg/L.

16. The method of claim 1, wherein the gas chromatograph and mass spectrometer have a detection limit for detecting and quantifying the concentration of the one or more N-nitrosamines in the aqueous solution, which is between 5.7 and 52 ng/L.

* * * * *